United States Patent [19]

Owens

[11] Patent Number: 4,502,471
[45] Date of Patent: Mar. 5, 1985

[54] STABILIZER FOR CERVICAL COLLAR
[75] Inventor: Troy R. Owens, Galveston, Tex.
[73] Assignee: Charles Greiner And Company, Inc., Westville, N.J.
[21] Appl. No.: 418,505
[22] Filed: Sep. 15, 1982
[51] Int. Cl.³ .............................................. A61H 1/02
[52] U.S. Cl. .................................... 128/75; 128/87 B; 128/78
[58] Field of Search .......................... 128/87 B, 75, 78

[56] References Cited

U.S. PATENT DOCUMENTS

| | | | |
|---|---|---|---|
| 3,724,452 | 4/1973 | Nitschke | 128/75 |
| 3,756,226 | 9/1973 | Calabrese | 128/75 |
| 4,289,122 | 9/1981 | Mason et al. | 128/89 R |
| 4,383,523 | 5/1983 | Schurman | 128/87 B |

Primary Examiner—Richard J. Apley
Assistant Examiner—David Isabella
Attorney, Agent, or Firm—Seidel, Gonda & Goldhammer

[57] ABSTRACT

A front piece adapted to overlie part of a person's chest is rigidly and removably connected to a front portion of a cervical collar. A rear piece adapted to overlie part of a person's back is rigidly and removably connected to a rear portion of a cervical collar. An adjustable strap interconnects the front and rear pieces.

11 Claims, 7 Drawing Figures

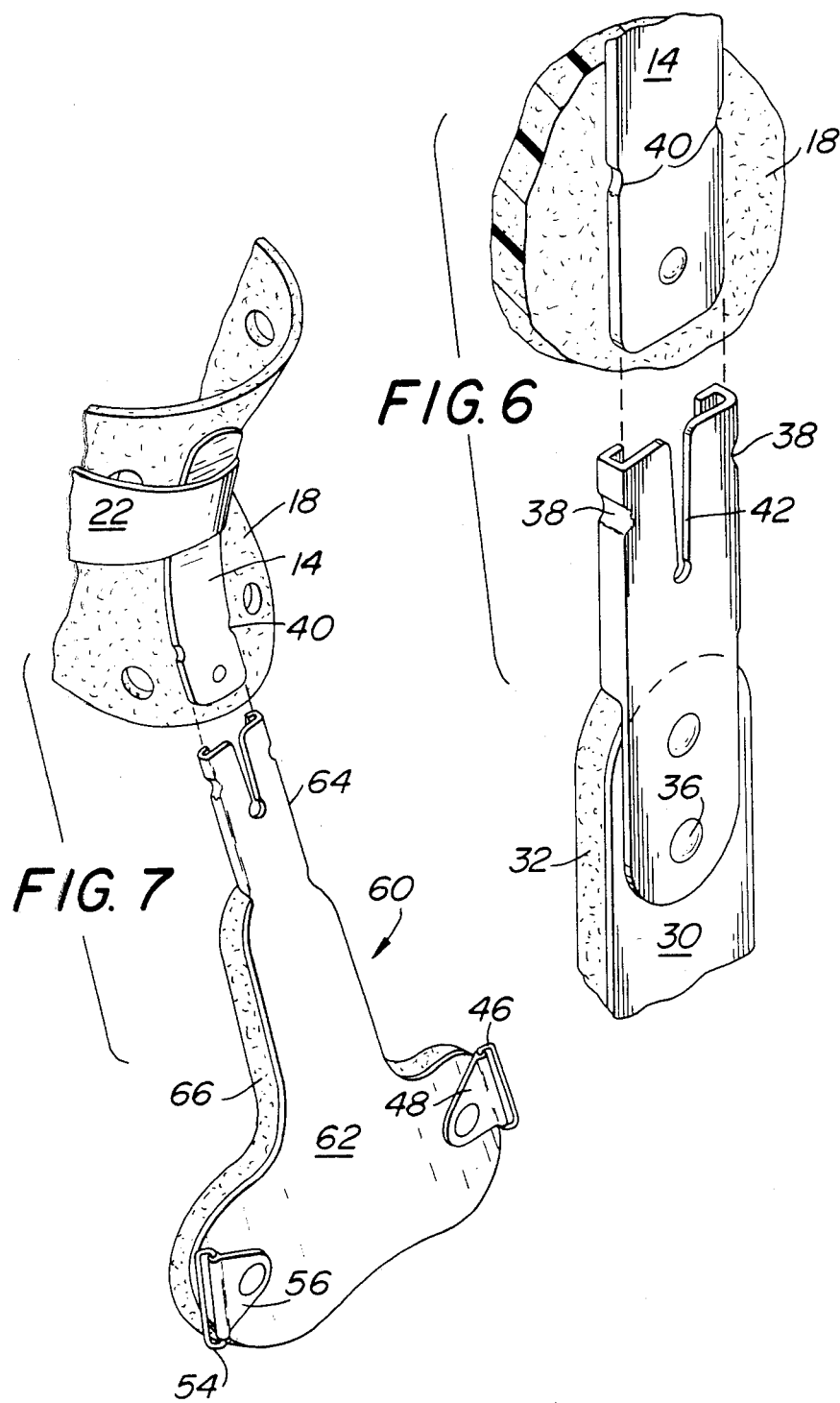

STABILIZER FOR CERVICAL COLLAR

BACKGROUND OF THE INVENTION

Cervical collars are well-known. See U.S. Pat. No. 3,756,226 issued to Anthony Calabrese on Sept. 4, 1973 and entitled Cervical Collar. The cervical collar disclosed in said patent is comprised of body halfs coupled together. Some injuries require more collar stability than others. Those injuries which require greater collar stability frequently alleviate over a short period of time whereby the amount of stability provided by the collar in said patent is sufficient.

The present invention is directed to solution of the problem of how to provide temporary stabilization for a cervical collar.

SUMMARY OF THE INVENTION

The present invention is directed to a stabilizer for a cervical collar. The stabilizer includes a front piece adapted to overlie part of a person's chest and a rear piece adapted to overlie part of a person's back. An adjustable strap means is provided for encircling a person's body and it removably innerconnecting said front piece with said rear piece. A means is provided on the upper end of each piece for rigidly and removably connecting each piece to a cervical collar. The stabilizer is adapted to be interrelated with the collar for that period of time where greater stability is needed. Thereafter, the stabilizer may be removed from the collar so that the collar may be worn in a normal manner.

It is an object of the present invention to provide a novel stabilizer which may be removably attached to a cervical collar.

Other objects and advantages will appear hereinafter.

For the purpose of illustrating the invention, there is shown in the drawings a form which is presently preferred; it being understood, however, that this invention is not limited to the precise arrangements and instrumentalities shown.

FIG. 6 is a an exploded view showing the connection between the cervical collar and the front piece of the stabilizer.

FIG. 7 is an exploded view of the front piece of a stabilizer and a portion of the collar in accordance with another embodiment of the present invention.

DETAILED DESCRIPTION

Figure 1:
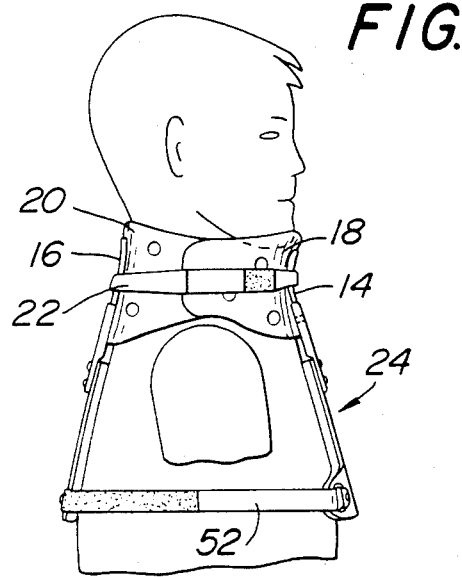
FIG. 1 is an elevation view of a person wearing a cervical collar with the extension of the present invention attached thereto.
Figure 4:
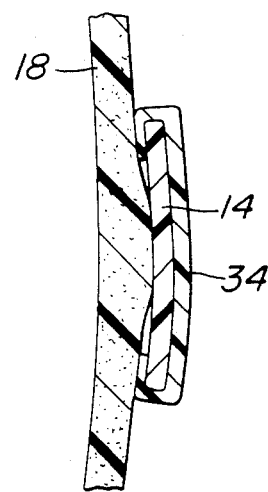
FIG. 4 is a sectional view taken along the line 4—4 in FIG. 3.

Referring to the drawing in detail, wherein like numerals indicate like elements, there is shown in FIG. 1 a cervical collar designated generally as 10 and provided with a stabilizer designated generally as 12. The stabilizer 12 may be utilized with a wide variety of collars. For purposes of illustration, the collar 10 is of the type disclosed in U.S. Pat. No. 3,756,226. Thus, the collar 10 includes a rigid reinforcing member 14 on a front half 18 and a rigid reinforcing member 16 on a rear half 20. The body halves 18 and 20 are coupled together by a strap means 22. The body halves 18 and 20 are preferably made from a soft flexible closed cell polymeric material and have a generally U-shape with the end portions on each body half being overlapped with one another as illustrated in the drawing.

The stabilizer 12 includes a front piece 26 adapted to overlie part of a person's chest and a rear piece 28 adapted to overlie part of a person's back. The front piece 26 and the rear piece 28 are identical except as will be made clear hereinafter. Hence, only the front piece 26 will be described in detail.

The front piece 26 includes a substrate 30 of rigid material having a generally T-shape. The substrate 30 is preferably made from a polymer plastic material such as ABS. A liner 32 is adhesively or otherwise secured to the curved inner surface of substrate 30. The liner 32 is preferably made from closed-cell foam polyethylene so as to have the following attributes: uniform thickness, non-toxic, low specific gravity of about 0.04, non-corrosive, and will not burn but will melt. The shape of liner 32 corresponds to the shape of substrate 30.

A connecting member 34 is fixedly connected to the center leg of substrate 30 in any convenient manner such as by rivets 36. The connecting member 34 is preferably made from a softer or more flexible plastic material than the substrate 30. Member 34 may be made from polyethylene.

Figure 5:
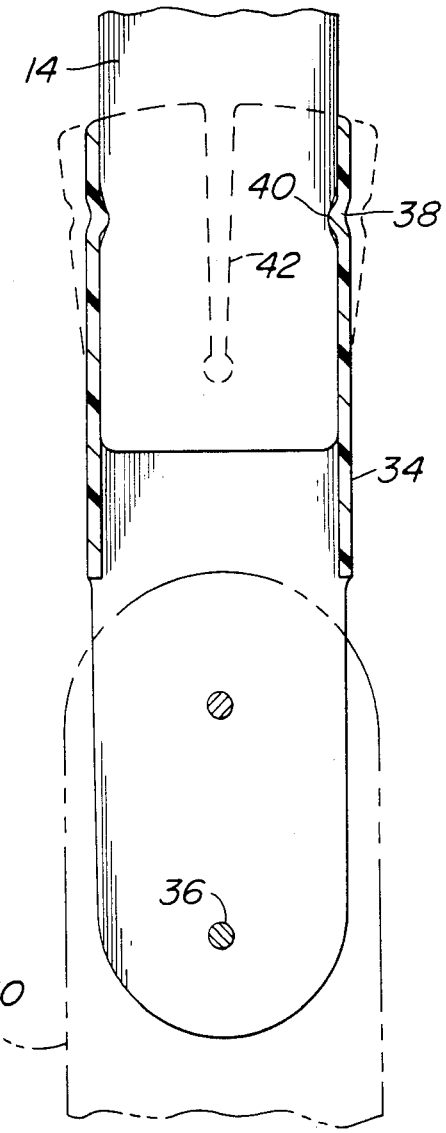
FIG. 5 is a sectional view taken along the line 5—5 in FIG. 3.
Figure 2:
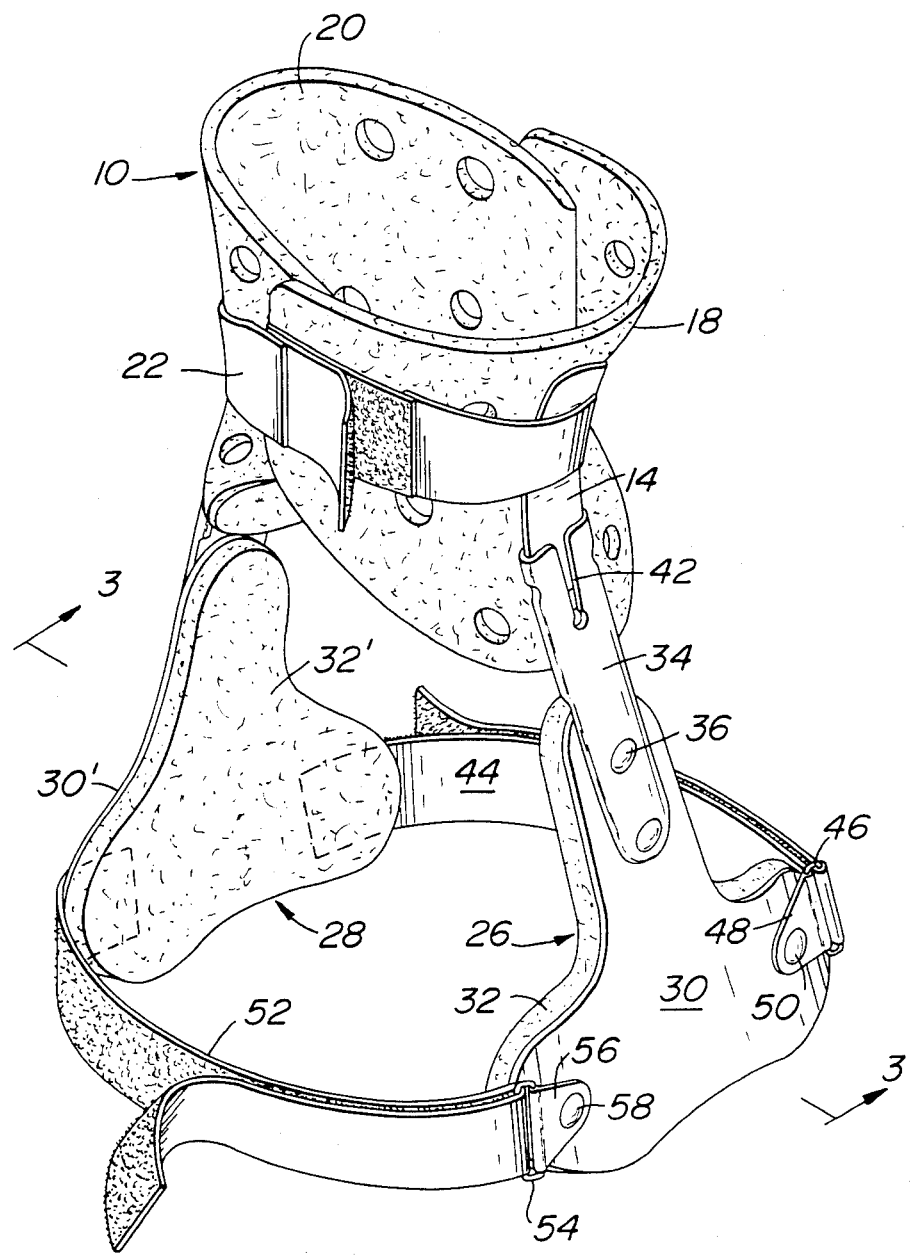
FIG. 2 is a perspective view of a cervical collar with the extension of the present invention attached thereto.
Figure 3:
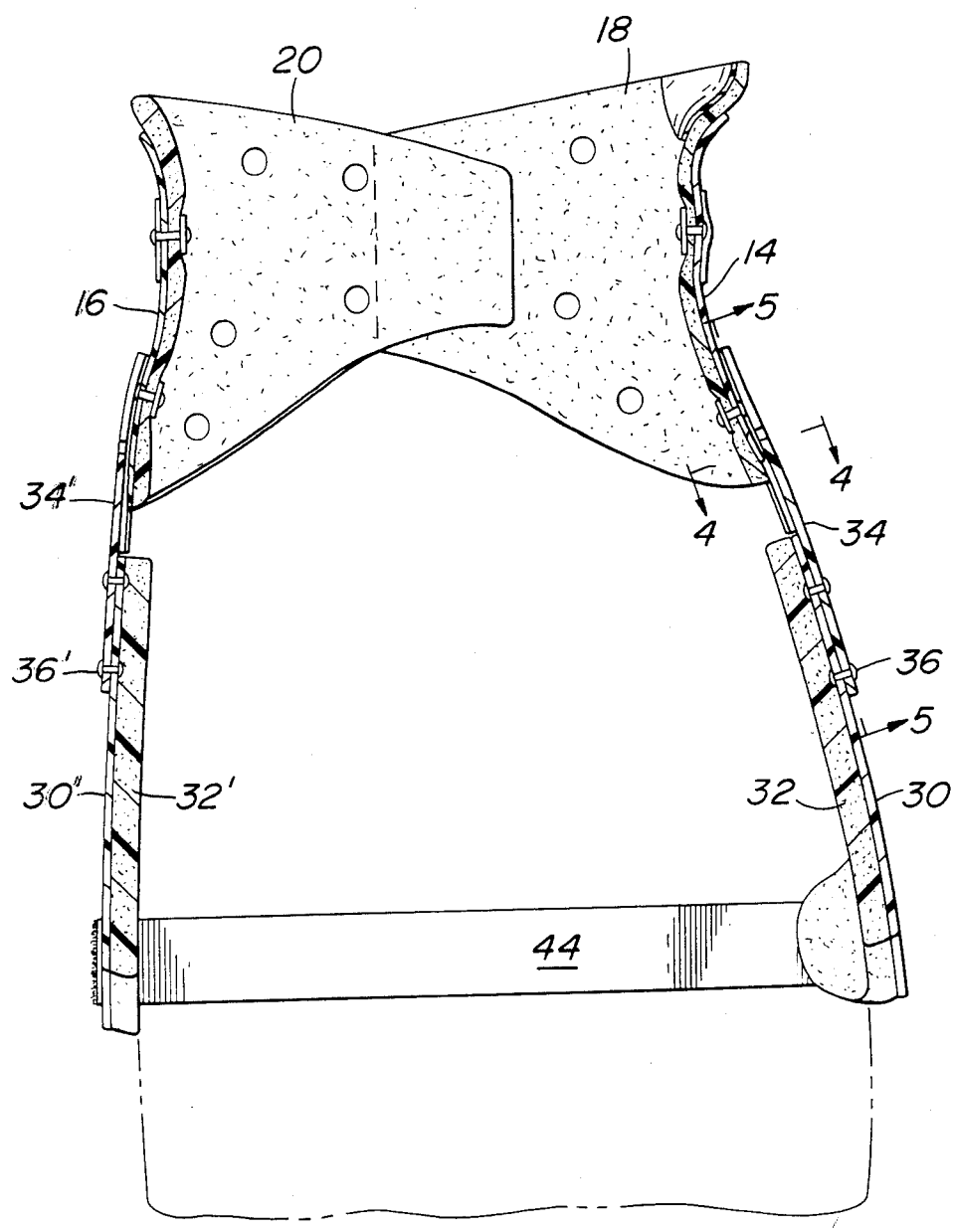
FIG. 3 is a sectional view taken along the line 3—3 in FIG. 2.

As shown more clearly in FIGS. 5 and 6, member 34 is channel-shaped at its upper end and has a pair of oppositely disposed projections 38 which extend toward one another. Each projection 38 is adapted to be received within a notch 40 on the reinforcing member 14. Member 34 is telescoped over member 14 until the projections 38 extend into the notches 40. Member 34 has a slot 42 to facilitate separation of members 14 and 34.

The stabilizer 12 is rigidly and removably attached to the collar 10 without the use of fasteners such as screws, rivets, snaps, etc. and at the same time facilitates separation in a manner which does not require any special tools. Thus, in order to separate member 34 from member 14, a screw driver, a key, or the like is inserted into the slot 42 and twisted so as to move the projections 38 away from one another to the phantom position shown in FIG. 5. Thereafter, forces applied in a downward direction to slide the member 34 off the end of member 14.

A strap 44 has one end fixedly secured to the substrate 30' on the rear piece 28. The strap 44 extends through a loop 46 on the front piece 26 and then overlies itself. Juxtaposed surfaces of the strap 44 are provided with adjustable fasteners which are preferably of the VELCRO type. The loop 46 is preferably supported by bracket 48 which in turn is secured to the substrate 30 in any convenient manner such as by rivet 50.

A strap 52 is similarly provided to interconnect the front and rear pieces 26, 28 respectively on the opposite side from the strap 44. One end of strap 42 is fixedly secured to the substrate 30'. An intermediate portion of strap 52 extends through loop 54 and then overlies itself with adjustable fasteners as described above. Loop 54 is supported by bracket 56 which in turn is secured to the substrate 30 by rivet 58.

In FIG. 7 there is illustrated another embodiment of the present invention wherein front piece 60 is removably and rigidly connected to member 14. Front piece 60 differs from front piece 26 in the following manner. The substrate 62 is integral in one piece with the connecting member 64. A foam liner 66, like liner 32, is applied to the inner surface of substrate 62. The front piece 60 is otherwise identical with front piece 26. A rear piece not shown and adapted to be used with front piece 60 is likewise provided with a connecting member integral in one piece with the substrate.

The collar 10 may be worn in a conventional manner. In connection with a particular injury, the collar 10 may need added stabilization. The front and rear pieces are attached to the collar 10 as described above. Thereafter, the front and rear pieces are coupled together by the straps 44, 52. If desired, one single strap may be utilized by innerconnecting the ends of the straps attached to the substrate 30'. When no longer needed, the front and rear pieces are disconnected while the collar 10 remains on the person for so long as required in accordance with medical advice.

The present inveantion may be embodied in other specific forms without departing from the spirit or essential attributes thereof and, accordingly, reference should be made to the appended claims, rather than to the foregoing specification, as indicating the scope of the invention.

I claim:

1. A stabilizing system comprising a body stabilizer and a self supporting cervical collar; said collar having U-shaped front and rear halves of soft flexible plastic with overlapping ends when encircling around a wearer's neck; and each half having a short rigid member thereon, said body stabilizer having a front piece adapted to overlie part of a person's chest and a rear piece adapted to overlie part of a person's back, adjustable strap means for encircling a portion of a person's body for removably interconnecting said front piece with said rear piece; and means on the upper end of said front and rear pieces for rigidly and removably connecting said front piece and rear piece respectively to said rigid members on said collar so that said front and rear pieces provide temporary support for said cervical collar and can be separated from said collar while said collar remains intact to support the wearer's neck.

2. A stabilizer in accordance with claim 1 wherein each means is constructed so as to telescope over its mating rigid member.

3. A stabilizer in accordance with claim 1 wherein each means includes mating projections on the upper ends of said pieces for entry into mating notches on one of said rigid members.

4. A stabilizer in accordance with claim 1 wherein each means includes a connecting member for connecting each piece to a collar half without use of discrete fasteners.

5. A stabilizer in accordance with claim 1 wherein each means includes a connecting member projecting upwardly from a generally T-shaped front piece, the terminal end of each connecting member having a longitudinally extending slot.

6. A stabilizer in accordance with claim 4 wherein the front and rear pieces include a rigid substrate integral in one piece with the connecting member.

7. A stabilizer in accordance with claim 4 wherein each piece includes a rigid substrate fixedly secured to the connecting member, the connecting member being softer than the substrate.

8. A stabilizer in accordance with claim 1 wherein each of said front and rear pieces includes a rigid substrate having a foam plastic liner on its inner surface.

9. A stabilizer in accordance with claim 1 wherein each means includes a projection at a side edge portion of the upper ends of said pieces and mating notches on the side edges of said rigid members.

10. An apparatus comprising a cervical collar and a stabilizer for temporary use with said cervical collar, said collar having a front and a back each having free end portions which overlap, a first rigid member on a central portion of said front, a second rigid member on a central portion of said back, said stabilizer including a front piece adapted to overlie part of a person's chest and a rear piece adapted to overlie part of a person's back, strap means coupling said front and back together, an adjustable strap means for encircling a portion of a person's body and for removably interconnecting said front piece with said rear piece, means on the upper end of said front piece for rigidly and removably connecting said front piece to said first rigid member without using any tools, and means on the upper end of said rear piece for rigidly and removably connecting the upper end of said rear piece to said second rigid member without using any tools.

11. A stabilizer for temporary attachment to a cervical collar comprising a front piece adapted to overlie a person's chest, a rear piece adapted to overlie a person's back, each of said pieces being generally T-shaped with the center leg extending upwardly, each of said pieces having a foam plastic liner on its inner surface, an adjustable strap means for interconnecting said front piece with said rear piece, and means on the upper end of each center leg for rigidly and removably connecting said front and rear pieces to a cervical collar in a temporary manner, said last mentioned means including a channel shape for each center leg, each channel shaped leg terminating at its upper end in a pair of projections, each projection being adapted to snap into a mating recess on a cervical collar without using any tools.

* * * * *